United States Patent
Orlowski et al.

[11] Patent Number: 5,965,632
[45] Date of Patent: *Oct. 12, 1999

[54] DENTAL CEMENT COMPOSITIONS

[75] Inventors: Jan A. Orlowski, Altadena; David V. Butler, West Covina; Jeffrey R. H. MacDonald, Pomona, all of Calif.

[73] Assignee: Scientific Pharmaceuticals Inc., Pomona, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/880,105

[22] Filed: Jun. 20, 1997

[51] Int. Cl.⁶ .................................................. A61K 6/083
[52] U.S. Cl. ...................... 523/116; 524/556; 524/558; 524/456; 524/494
[58] Field of Search ........................... 523/116; 524/556, 524/558, 456, 494

[56] References Cited

U.S. PATENT DOCUMENTS

| | | | |
|---|---|---|---|
| 4,808,228 | 2/1989 | Randklev | 523/116 |
| 5,063,257 | 11/1991 | Akahane et al. | 523/117 |
| 5,151,453 | 9/1992 | Ibsen et al. | 523/116 |
| 5,152,762 | 10/1992 | Mitra et al. | 523/116 |
| 5,367,002 | 11/1994 | Huang et al. | 523/116 |
| 5,382,284 | 1/1995 | Arnold | 106/35 |
| 5,520,725 | 5/1996 | Kato et al. | 523/116 |
| 5,520,922 | 5/1996 | Gasser et al. | 523/116 |

*Primary Examiner*—Andrew E. C. Merriam
*Attorney, Agent, or Firm*—Evan M. Kent; Stewart L. Gitler

[57] ABSTRACT

A two paste glass ionomer type dental cement system, with both pastes being, preferably, of similar consistency. The first paste represents primarily a suspension of an inert filler in a water solution of polyacrylic acid, or its copolymers with other ethylenically unsaturated acids, having molecular weight of 25,000 to 100,000 and, optionally, various additives, such as filler suspending agents, coloring agents, agents influencing working/setting time (retardants or accelerators), Theological agents, pH modifiers, etc. The other paste represents primarily a particulate glass flux containing silicon and aluminum oxides, calcium fluoride and, optionally, other inorganic salts, including aluminum phosphate, and sodium, barium and aluminum fluorides, suspended in a liquid medium consisting primarily of a water solution of a hydrophilic acrylic monomer or polymer. In order to achieve a desirable consistency, organic or inorganic thickening agents may be added in suitable quantities.

20 Claims, No Drawings

DENTAL CEMENT COMPOSITIONS

BACKGROUND OF THE INVENTION

1. Field of the Invention

This invention relates to the field of dental cement compositions, and in particular to two-component glass ionomer type dental cements which are novel in form, composition, and method of handling, featuring improved strength, handling, and reproducibility of properties over conventional glass ionomer cements.

2. Background of the invention

Prior art glass ionomer cements are formulated as a two-part system, one part being in a liquid form and the other in a powder form. The liquid is typically a solution of oligomers or copolymers of acrylic acid. The molecular weight of such polymers is usually in the range of 40,000 to 50,000, and their concentration may vary from about 40% to 60%. The powder is composed of fine alkaline glass particles, and its chemical composition includes, as essential ingredients, silicon and aluminum oxides, calcium fluoride, and modifying additives which may include aluminum, sodium or barium fluorides, alkaline metals or alkaline earth oxides, aluminum phosphate, zinc, zirconium, and titanium oxides.

Powder/liquid systems are the least desirable forms of self (chemically) cured dental cements and restoratives. Maintaining the proper proportion between the two components of a two-part cement system is, in the case of glass ionomers, critical for achieving acceptable reproducibility of the relevant characteristics of the cured material. However, it is extremely difficult to meet such a requirement with powder/liquid systems, taking into consideration the small amounts of materials involved in the preparation of mixes for dental applications and the imprecise tools used for these purposes.

Moreover, dental assistants and clinicians are accustomed to other powder/liquid type cements and restoratives which do not require a high level of precision in dispensing, and have little understanding of the difference in requirements when glass ionomer type materials are involved. Imprecise dispensing may, however, have a detrimental effect on the mechanical properties, resistance to the oral environment, curing characteristics, ability to bond to dentin and tooth enamel, and tissue compatibility of glass ionomer cements.

Generally, an excess of liquid will result in slower setting cements which are more susceptible to deterioration when exposed to saliva and more likely to irritate pulp and mucosa. Also, due to their light consistency, such mixes are unsuitable for applications requiring firmer consistencies and greater mechanical strength.

An excess of powder causes mixes to be too dry and may not allow sufficient working time. The consistency of such mixes may make them unsuitable in applications where flowability of the mix is mandatory, such as in a capacity as cavity liners, orthodontic band cements, and crown and bridge cements. Also, after cure, such cements are likely to be excessively brittle and their ability to bond to the tooth structure will be impaired.

Minor variations in the characteristics of the liquid or powder, such as variations in the molecular weight of the polyacrylic acid and particle size of the glass, may make the originally designed dispensing system unsuitable. Moreover, changes in ambient temperature influence the viscosity and surface tension of the liquid and, consequently, affect the powder/liquid ratio because of variations in drop sizes when dispensed in the customary way from dropper-type bottles. The usual way of dispensing powder by scoop represents an intrinsically imprecise method because the bulk density of the powder may vary with time due to settling and the way the powder is handled (shaking, vibration, pounding, etc.). All these factors may significantly affect the properties and, in some instances, the safety of the cements to such a degree that their suitability for an intended purpose may be questionable.

Additional problems related to variations in the particle size of the powder may also be encountered. Manufactured batches of powders consist of difficult to reproduce blends of particles of different sizes. Variations in the distribution of particle sizes are virtually unavoidable within batches of commercial products. Larger particles tend to migrate to the bottom of the container, leaving smaller particles on top. Using the same dispensing system for powders consisting of different-sized particles will result in mixes of varying consistencies and unpredictable working and setting times. It is generally recognized that smaller sized glass particles will shorten the working time and result in mixes characterized by denser consistencies.

A common characteristic of glass ionomer compositions is their undesirably short working time. In order to assure the best properties of the cured cement, mixing of the components and application should be accomplished before the blend starts to show signs of setting. However, preparation of powder/liquid mixes is time-consuming, leaving clinicians with little latitude to complete the application within the allowed working time for the cement.

Powder/liquid systems are also undesirable from the point of view of economy because substantial waste of the material is unavoidable. Dispensing cannot be accomplished in a way which closely approximates the amount of material the clinician needs. Usually, a large part of the cement is wasted.

To alleviate the shortcomings of powder/liquid versions of glass ionomers, a solution has been offered, derived from a technique used in packaging more expensive brands of dental amalgams. This system is comprised of a two-compartment capsule, separated by a breakable diaphragm. One of the compartments is filled with a measured amount of the powder, and the other with the liquid component of the glass ionomer cement. After the diaphragm is broken, the capsule is vigorously shaken using a vibrator-type machine for a specified period of time, producing relatively homogeneous mixes of more consistent quality. This solution eliminates some of the shortcomings of conventionally dispensed two-part glass ionomer cements, assuring better reproducibility of the properties of the cured cements and simplifying handling. However, it dramatically increases the cost per application and further increases waste. Also, handling of the material, although much easier when compared to individually dispensing the powder and liquid components, still remains complex, and the working time remaining after removal of the capsules from the vibrator is unconveniently short.

Attempts to formulate glass ionomer cements in a different form than the conventional powder/liquid system were, up to now, unsuccessful. The major advantages of glass ionomers in clinical applications are their ability to bond to the tooth structure, without the necessity of acid etching, and to protect the tooth structure from decay because they provide a sustained release of fluoride. Preservation of these characteristics, combined with the need to meet requirements related to mechanical strength, curing characteristics and safety, has imposed severe restrictions on the chemical composition of the cement components, their concentration, molecular weight, and physical form. These factors also severely limited freedom in incorporating various additives which, although highly desirable otherwise, were believed to have a detrimental effect on the properties of the cement, because of the necessity of operating in a narrow range of parameters and sensitivity of the fundamental components to even minor changes in their chemical composition, physical form, and concentration in the final mix.

Efforts have been undertaken to change the physical form of commercial glass ionomer cements in order to make them more convenient to use, which resulted in modifications of their compositions. These modified cements, while encompassing some of glass ionomer's fundamental components, have differed, however, from the original concept of glass ionomers in important aspects, including their basic chemistry and curing mechanism. Consequently, the major advantages of glass ionomers, including their ability to bond to the tooth structure, to maintain a high level of Fluoride release, and to prevent tooth decay, were severely compromised.

Most common examples of such modified formulations are comprised of blends of methacrylate monomers with glass ionomer-type powders used as fillers. They represent light-cured one-component or self- (chemically-) cured two component systems. Their mechanism of cure relies, however, on chain-forming of ethylenically unsaturated methacrylate monomers, while the curing of glass ionomers depends on the reaction of the carboxylic group present in polyacrylic acid with alkaline sites of glass powder. This distinctive mechanism of cure and the presence of water in glass ionomer formulations are critical to preserving their main advantages: their ability to bond to an unconditioned tooth structure and to provide sustained Fluoride release.

Some prior publications relating to the field of this invention include the following U.S. Pat. No. 5,520,922 issued May 28, 1996 to Gasser, Oswald and Guggenberger, Rainer; U.S. Pat. No. 5,520,725 issued May 28, 1996 to Kato Shin-Ichi et al.; U.S. Pat. No. 5,382,284 issued Jan. 17, 1995 to Thomas J. Arnold; U.S. Pat. No. 5,367,002 issued Nov. 22, 1994 to Huang Chin-Teh et al; and U.S. Pat. No. 5,063,253 issued Nov. 5, 1991 to Akahane Shoji et al.

SUMMARY OF THE INVENTION

The object of the present invention is provide a novel glass ionomer cement comprised of two pastes, one of which represents primarily a blend of a polyacrylic acid solution in water with inert fillers or thickeners. The other paste consists of a suspension of alkaline glass particles in a liquid medium containing hydrophilic acrylate, preferably methacrylate, monomers and having a consistency which is thick enough to maintain the glass particles in suspension. Compositions of this invention preserve all characteristics of conventional glass ionomer cements, including their basic chemistry and curing mechanism and, consequently, their ability to bond to the tooth structure and to provide sustained Fluoride release. However, they allow for a dramatic improvement in ease of handling, precision in dispensing, reproducibility of chemical, physical, and biological characteristics of the cured cement, and reduction of waste, as well as alleviate concern about the possibility of pulp damage or irritation of mucosa.

This development was made possible by finding additives which, if used at judicious concentrations, allow for the formulation of the two parts of the cement in a paste form, while not negatively affecting (in fact, often positively affecting) the properties of the cured cement and providing excellent storage stability. Critical requirements in the formulation of such a material are the selection, concentration, and balance of additives, as well as the concentration of the basic components. This represents the discovery on which this invention is based.

In this invention, the term "paste" describes a material of a semi-solid consistency, able to maintain its physical form for a period of time if mechanical forces are not applied to it, but able to change its form when subjected to mechanical forces. Such pastes may consist of mixes of liquid with fine solid particles or gels or blends thereof. It is desirable, but not critical, that the two pastes of the cements of this invention exhibit similar consistency and are extruded through orifices whose cross-sectional areas are the same or whose ratios are pre-determined. This will provide for better control over the ratios of the amounts dispensed and allow for the ratio of the pastes to be varied, if desired, in a controlled manner.

The present invention eliminates the main shortcomings of prior art two-part dental cements. It facilitates handling, allows for longer working time, and is economical to use because it greatly reduces waste. Because of the physical form of the components, the amounts and proportions of dispensed material may be controlled with accuracy, assuring good to excellent reproducibility of the properties of the cured cement. Desirable curing characteristics of the cement are, therefore, assured, as well as its reproducibility of the consistency, ease of handling, biocompatibility, resistance to the oral environment, and good mechanical properties. If the two components of the cement are in the form of pastes of similar consistency and are dispensed from containers through orifices of defined sizes, their proportions may easily be controlled, without using any instruments or other devices, by the length of the dispensed material.

This invention provides glass ionomer type dental cements which are novel in form, composition, and method of handling. It allows for formulating cements featuring improved strength, handling, and reproducibility of properties over the conventional glass ionomer cements. Prior art glass ionomer cements represented a two-component powder and liquid system, which is difficult to mix, to proportion the components accurately, and, consequently, to control some of the most relevant characteristics of the material, including working and setting time, pH, mechanical strength, consistency, and resistance to oral fluids. The cement of present invention is a two paste system, with both pastes being, preferably, of similar consistency.

The first paste represents primarily a suspension of an inert filler in a water solution of polyacrylic acid, or its copolymers with other ethylenically unsaturated acids, having a molecular weight of 25,000 to 100,000 and, optionally, various additives such as filler suspending agents, coloring agents, agents influencing working/setting time (retardants or accelerators), rheological agents, pH modifiers, etc.

The second paste represents primarily a particulate glass flux containing silicon and aluminum oxides, calcium fluoride and, optionally, other inorganic salts, including aluminum phosphate, and sodium, barium and aluminum fluorides, suspended in a liquid medium consisting primarily of a hydrophilic acrylic monomer or polymer. In order to achieve a desirable consistency, organic or inorganic thickening agents, including silicon and aluminum oxides and their salts or polymers, such as polymers or copolymers of polyacrylic acid, ethylene oxide or vinyl alcohol, cellulose derivatives, organic gums, etc., may be added in suitable quantities.

DETAILED DESCRIPTION OF THE PREFERRED EMBODIMENTS

The general description of the composition of the cements of this invention is characterized below.

It will be understood that all part percentages expressed in the description to follow are weight percentages. Similarly, all molecular weights expressed herein are average weights of the compound of concern.

In a generally broad embodiment of the invention, the first paste, hereinafter referred to as Part A paste, comprises the following ingredients:

a) 50 to 95% of 45 to 80% polyacrylic acid solution in water, such polyacrylic acid solution having a molecular weight of 35,000 to 65,000;

b) 2 to 40% of inorganic filler having an average particle size of 40 microns or less; and c) optionally, various additives, such as coloring agents, rheological agents, stabilizers, surface active agents, and cure time controlling agents.

The second paste, hereinafter referred to as Part B paste, comprises the following ingredients:

a) 60 to 92% of alkaline glass having an average particle size of 1 to 25 microns, whose chemical composition includes silicon oxide, aluminum oxide, and calcium, strontium, barium, or lanthanum fluorides;

b) 8 to 40% of a 0.1 to 50% solution of a water-soluble acrylate or methacrylate monomer, or a polymer of such a monomer; and c) optionally, water and various additives, such as those mentioned above in the description of Part A paste.

It will be understood by those skilled in the art that cements of this invention may differ substantially in many respects, including consistency of the pastes, working and setting times, appearance, method of dispensing, optimal proportions of the Part A and B pastes in mixes, mechanical characteristics, chemical resistance to different environments, to name a few.

Prior to this invention, it was believed that conventional glass ionomer cements, i.e., cements in which the basic chemistry and curing mechanism are fully preserved, might not be formulated in a form other than powder/liquid, without sacrificing their essential characteristics, including storage stability, mechanical properties, chemical resistance, and controllable, clinically acceptable working/setting times. Maintenance of the concentration of polyacrylic acid in a narrow range in the glass ionomer liquid, dryness of the glass, and absence of other fillers at significant concentrations were considered necessary conditions to assure acceptable physical and chemical properties of the cements, as well as their acceptable handling characteristics and clinical performance.

It was, therefore, astonishing to find that the liquid as well as the powder parts of conventional glass ionomer cements can be substantially modified without negatively affecting, but rather enhancing, the most relevant characteristics of the cured product.

Addition of certain fillers, particularly quartz, which are chemically resistant (inert) to the milieu of polyacrylic acid, alone or in conjunction with other additives, combined with increasing the concentration of the polyacrylic acid to 50 to 75%, allowed for the formulation of the first part (Part A) of the cement in a paste form.

It was also found that a fully functional second part paste (Part B) may be formulated by adding 15% or less of hydrophilic acrylate monomers or their water solutions and thickening/rheological agents to the conventional glass ionomer powder. Examples of such thickening/rheological agents include, but are not limited to, polycarboxylic acids and its copolymers, preferably having a molecular weight above 200, hydrophilic silica, polyhydroxyalkylacrylates or methacrylates, xanthan and cellulose derivatives and other water soluble gums, polyvinyl pyrollidone, polyvinyl alcohol, and polyethylene oxide.

Other additives which may be incorporated into either part of the cement are colorants (dyes or pigments), humectants to prevent drying of the material in their containers, and cure retardants or accelerators of the type commonly used in the industry in the formulation of glass ionomer cements and other polymeric medical or dental devices.

A preferred embodiment of the Part A paste of the cement, according to this invention, comprises:

a) 60 to 80% of a water solution of polyacrylic acid or copolymers of acrylic acid with maleic or itaconic acids, having molecular weight of 40,000 to 60,000;

b) 4 to 40% of inorganic filler selected from the group consisting of quartz, glass, silicon oxide, aluminum oxide, zirconium oxide, and blends thereof; and c) 5% or less of thickening/rheological agents. Preferred thickening/rheological agents are hydrophilic silica and polyacrylic acid, or copolymers of acrylic acid with other ethylenically unsaturated carboxylic acids or alcohols, having a molecular weight of 100,000 to 500,000.

A preferred embodiment of the Part B paste of the cement, according to this invention, comprises:

a) 65 to 85% of alkaline glass particles having an average particle size of 3 to 40 microns, 95% of such particles having a particle size below 60 microns;

b) 10 to 35% of a 0.2 to 20% solution of hydrophilic acrylic monomers or polymers of such monomers (preferred are monomers or polymers of hydroxyethylmethacrylate hydroxypropylmethacrylate, and acrylic and methacrylic acid); and c) 10% or less of thickening/rheological agents. The most preferred thickening/rheological agents are hydrophilic silica and polyacrylic acid, or copolymers of polyacrylic acid with other ethylenically unsaturated carboxylic acids or alcohols having a molecular weight of 200,000 to 300,000.

For better control of the uniformity of mixes, it is desirable that Part A and Part B are of contrasting color. Also, for certain dental applications, the availability of cements in tooth shades is advantageous. Such requirements can be easily met by incorporating coloring agents (pigments and dyes), acceptable for intra-oral use, into one or both parts of the cement. Preferred coloring agents for the cements of this invention are pigments based on iron oxides.

EXAMPLES OF FORMULATIONS AND PROPERTIES OF THE CEMENTS OF THIS INVENTION

Examples of formulations and properties of the cements of this invention are given below. These examples are provided for the purpose of illustration and for better understanding of the basic concept of the invention. They are presented, however, with no intention of fully encompassing its range and scope.

Example 1

The glass ionomer cement was formulated as follows, with % by weight given for each ingredient.

The Part A paste comprised:

| | |
|---|---|
| 67% water solution of polyacrylic acid having molecular weight of approximately 50,000 | 61% |
| powdered quartz having an average particle size of 7 microns | 38% |
| silica | 1% |

The Part B paste comprised:

| | |
|---|---|
| glass ionomer powder containing 30% $SiO_2$, 24% $CaF_2$, 13% $Al_2O_3$, the balance consisting of $AlF_3$, $BaSO_4$, and $AlPO_4$ | 71% |
| hydroxyethyl methacrylate | 1.4% |
| water | 27.5% |
| iron oxide | 0.1% |

These two pastes were mixed together in volumetrically equal proportions. The material was workable at 23° C. for 110 seconds and cured in 240 seconds. Its compressive strength was 6000 psi (43 MPa).

Example 2

The glass ionomer cement was formulated as follows:
The Part A paste comprised:

| | |
|---|---|
| 67% water solution of polyacrylic acid having molecular weight of approximately 50,000 | 92% |
| sub-micron hydrophilic silica | 5% |
| aluminum oxide | 1.5% |
| polyacrylic acid having a molecular weight of approximately 200,000 | 1.5% |

The composition of the Part B paste was identical to that described in Example 1 above.

These two pastes were mixed together in volumetrically equal proportions. The material was workable at 23° C. for 100 seconds and cured in 220 seconds. Its compressive strength was 8200 psi (57 MPa).

Example 3

The glass ionomer cement was formulated as follows:
The Part A paste comprised:

| | |
|---|---|
| 62% water solution of polyacrylic acid having molecular weight of approximately 45,000 | 64% |
| powdered quartz having an average particle size of 10 microns | 26% |
| barium boroaluminosilicate glass having an average particle size of 5 microns | 9% |
| sub-micron silica | 1% |

The Part B paste comprised:

| | |
|---|---|
| glass ionomer powder, as described in Example 1 | 68% |
| water | 29.5% |
| hydroxypropyl methacrylate | 2.5% |

These two pastes were mixed together in volumetrically equal proportions. The material was workable at 23° C. for 120 seconds and cured in 300 seconds. Its compressive strength was 11,600 psi (83 MPa).

Example 4

The glass ionomer cement was formulated as follows:
The composition of the Part A paste was identical to that described in Example 3 above.
The Part B paste consisted of:

| | |
|---|---|
| glass ionomer powder, as described in Example 1 | 70.26% |
| water | 28.18% |
| hydroxyethyl methacryiate | 1.50% |
| polyacrylic acid having a molecular weight of approximately 200,000 | 0.06% |

These two pastes were mixed together in volumetrically equal proportions. The material was workable at 23° C. for 85 seconds and cured in 340 seconds. Its compressive strength was 15,000 psi (103.3 MPa).

Example 5

The glass ionomer cement was formulated as follows:
The composition of the Part A paste was identical to that described in Example 3 above.
The Part B paste consisted of:

| | |
|---|---|
| glass ionomer powder, as described in Example 1 | 69.30% |
| water | 24.60% |
| hydroxyethyl methacrylate | 6.10% |

These two pastes were mixed together in volumetrically equal proportions. The material was workable at 23° C. for 90 seconds and cured in 360 seconds. Its compressive strength was 10,000 psi (69.4 MPa).

Example 6

The glass ionomer cement was formulated as follows:
The composition of the Part A paste was identical to that described in Example 3 above.
The Part B paste consisted of:

| | |
|---|---|
| glass ionomer powder, as described in Example 1 | 72.06% |
| water | 27.88% |
| polyacrylic acid having a molecular weight of approxiinately 200,000 | 0.06% |

These two pastes were mixed together in volumetrically equal proportions. The material was workable at 23° C. for 80 seconds and cured in 370 seconds. Its compressive strength was 13,400 psi (92.4 MPa).

Example 7

The glass ionomer cement was formulated as follows:
The composition of the Part A paste was identical to that described in Example 3 above.
The Part B paste consisted of:

| | |
|---|---|
| glass ionomer powder, as described in Example 1 | 70.425% |
| water | 29.425% |
| hydroxyethyl methacrylate | 0.150% |

These two pastes were mixed together in volumetrically equal proportions. The material was workable at 23° C. for 90 seconds and cured in 360 seconds. Its compressive strength was 14,000 psi (96.6 MPa).

Various changes and modifications may be made to Applicant's invention as would be apparent to those skilled in the art. However, these changes or modifications are included in the teaching of Applicant's disclosure, and it is intended that the invention be limited only by the scope of the claims appended hereto.

What is claimed is:

1. An ionomeric curing dental cement composition:
   a first paste composition comprising:
   from 50 to 95% by weight of an aqueous solution of a polyacrylic acid polymer or a polyacrylic acid copolymer with ethylenically unsaturated acids; and
   from 2 to 40% by weight of an inorganic filler having an average particle size of 40 microns or less; and
   a second paste component comprising:
   a suspension of from 60 to 92% by weight alkaline glass particles having an average particle size from 1 to 25 microns;
   from 8 to 40% by weight of an aqueous liquid medium thickened to a point where sedimentation will not occur and
   wherein an acidic thickener is present in an amount where sedimentation will not occur.

2. The composition of claim 1, wherein said inorganic filler is selected from the group consisting of quartz, glass, aluminum oxide, silica, and a blend thereof.

3. The composition of claim 1, wherein said solution of polyacrylic acid of said first paste has a viscosity based average molecular weight of from 35,000 to 65,000.

4. The composition of claim 1, wherein said polyacrylic acid copolymer is a polyacrylic acid with said ethylenically unsaturated acids selected from the group consisting of maleic acid, itaconic acid and combinations thereof.

5. The composition of claim 1, wherein said aqueous acrylic monomer is selected from the group consisting of hydroxyethyl methacrylate or acrylate, hydroxy-n-propyl methacrylate or acrylate, hydroxy-isopropyl methacrylate or acrylate, hydroxybutyl methacrylate or acrylate, hydroxy-isobutyl methacrylate or acrylate, and mixtures thereof.

6. The composition of claim 2, wherein a thickening polyacrylic acid component of said second paste is a polymer or copolymer of acrylic or methacrylic acid.

7. The composition of claim 1, wherein said second paste further comprises 10% or less powdered inert glass, quartz, aluminum oxide, silica, or a blend thereof.

8. The composition of claim 1, wherein said first paste or said second paste further comprises a thickening agent selected from the group consisting of alkyl-cellulose, hydroxyalkyl-cellulose, Guar gum, Agar gum, Arabic gum, Ghath gum, Keroga gum, Tragacanth gum, Xanthan gum, Tamarind gum, Locust Bean Gum, pectins, polyacrylamide, polyhydroxy ($C_1$–$C_4$) alkyl methacrylate, polyhydroxy ($C_1$–$C_4$) alkyl acrylate, polyethylene glycol, polyethylene oxide, polyvinyl pyrrolidone, polyvinyl alcohol, and starch.

9. The composition of claim 1, wherein said first paste or said second paste further comprises 10% or less of a hydrophilic silica, having an average particle size of 2 microns or less.

10. The composition of claim 1, wherein said alkaline glass particles form a glass flux comprising silicon oxide, aluminum oxide, and a metal fluoride selected from the group consisting of strontium fluoride, calcium fluoride, barium fluoride, or lanthanum fluoride.

11. An lonomeric dental cement composition comprising:
    a first paste component comprising:
    from 60 to 80% by weight of an aqueous solution of a polyacrylic acid or a polyacrylic acid copolymer with ethylenically unsaturated acids, said polyacrylic acid solution having a viscosity based average molecular weight of from 40,000 to 60,00; and
    a second paste component comprising:
    a suspension of from 65 to 85% by weight of an alkaline glass flux, having an average particle size of 3 to 40 microns; and
    from 10 to 35% 6 by weight of an aqueous liquid medium of an acrylate or methacrylate monomer, or a polymer of such a monomer; and
    where said aqueous liquid medium is thickened by an acidic thickener to a point where sedimentation will not occur.

12. The dental cement composition of claim 11, wherein said ethylenically unsaturated acid is a maleic acid, an itaconic acid or a combination thereof.

13. The dental cement composition of claim 11, wherein said inorganic filler is selected from the group consisting of quartz, glass, silicon oxide, aluminum oxide, zirconium oxide, and blends thereof.

14. The dental cement composition of claim 11, further comprising up to 5% by weight of a thickening/rheological agent in said first paste component selected from the group consisting of hydrophilic silica, polyacrylic acid and copolymers of polyacrylic acid with ethylenically unsaturated carboxylic acids having a viscosity based average molecular weight of 100,000 to 500,000.

15. The dental cement composition of claim 11, wherein said hydrophilic acrylic monomers or copolymers of such monomers of said second paste component is selected from the group consisting of hydroxyethyl methacrylate and hydroxypropyl-methacrylate.

16. The dental cement composition of claim 11, further comprising up to 10% by weight of a thickening rheological acid in said second paste component selected from the group consisting of hydrophilic silica, polyacrylic acid and copolymers of polyacrylic acid with ethylenically unsaturated carboxylic acids or esters having a viscosity based average molecular weight of 200,000 to 500,000.

17. The ionomeric curing dental cement composition of claim 1, wherein said second paste further comprises a hydrophilic methacrylate monomer.

18. The ionomeric curing dental cement composition of claim 17, wherein said hydrophilic methacrylate monomer is hydroxyethyl methacrylate or hydroxypropyl methacrylate.

19. The ionomeric curing dental cement composition of claim 17, wherein said hydrophylic methacrylate monomer is present in a concentration of up to 10% by weight of said aqueous liquid medium of said second paste.

20. An ionomeric curing dental cement composition:
    a first paste composition comprising:
    from 50 to 95% by weight of an aqueous solution of a polyacrylic acid polymer or a polyacrylic acid copolymer with ethylenically unsaturated acids; and
    from 2 to 40% by weight of an inorganic filler having an average particle size of 40 microns or less; and
    a second paste component comprising:
    a suspension of from 60 to 92% by weight alkaline glass particles having an average particle size from 1 to 25 microns; and
    from 8 to 40% by weight of an aqueous liquid medium thickened to a point where sedimentation will not occur, wherein said aqueous liquid medium of said second paste comprises a thickener consisting of less than 0.06 weight percent polyacrylate acid and/or copolymers of polyacrylate acid having a viscosity based molecular weight of 200,000 to 500,000.

* * * * *